(12) United States Patent
Pedrizzetti et al.

(10) Patent No.: US 11,559,691 B2
(45) Date of Patent: Jan. 24, 2023

(54) METHOD AND DEVICE FOR CARDIAC ELECTRIC SYNCHRONIZATION

(71) Applicant: Amid srl, Sulmona (IT)

(72) Inventors: Gianni Pedrizzetti, Prato (IT); Giovanni Tonti, Sulmona (IT)

(73) Assignee: Amid srl, Sulmona (IT)

( * ) Notice: Subject to any disclaimer, the term of this patent is extended or adjusted under 35 U.S.C. 154(b) by 0 days.

(21) Appl. No.: 16/824,874

(22) Filed: Mar. 20, 2020

(65) Prior Publication Data
US 2020/0215332 A1  Jul. 9, 2020

Related U.S. Application Data

(63) Continuation of application No. PCT/EP2017/025269, filed on Sep. 23, 2017.

(51) Int. Cl.
*A61N 1/365* (2006.01)

(52) U.S. Cl.
CPC ..... *A61N 1/36585* (2013.01); *A61N 1/36528* (2013.01); *A61N 1/36564* (2013.01); *A61N 1/36578* (2013.01)

(58) Field of Classification Search
CPC ............ A61N 1/36585; A61N 1/36528; A61N 1/36564; A61N 1/36578; A61N 1/3684; A61N 1/3627; A61B 8/06
See application file for complete search history.

(56) References Cited

U.S. PATENT DOCUMENTS

| 5,947,903 A | 9/1999 | Ohtsuki et al. |
| 8,858,437 B2 | 10/2014 | Pedrizzetti et al. |
| 9,349,178 B1 * | 5/2016 | Itu ........................... G16H 50/50 |
| 2007/0083116 A1 * | 4/2007 | Sato ........................ A61B 8/00 600/437 |
| 2007/0299479 A1 * | 12/2007 | Saksena ................. A61N 1/368 607/18 |

(Continued)

OTHER PUBLICATIONS

Pedrizzetti G, Arvidsson PM, Töger J, Borgquist R, Domenichini F, Arheden H, Heiberg E. On estimating intraventricular hemodynamic forces from endocardial dynamics: A comparative study with 4D flow MRI. J Biomech. Jul. 26, 2017;60:203-210. Epub Jul. 5, 2017. PMID: 28711 (Year: 2017).*

(Continued)

*Primary Examiner* — Gary Jackson
*Assistant Examiner* — Alexander M Eisenberg
(74) *Attorney, Agent, or Firm* — Woodard, Emhardt, Henry, Reeves & Wagner, LLP (57) ABSTRACT

The disclosure relates to a method for improving pacing settings of a pace maker, comprising:
  receiving a set of pacing settings for the pace maker;
  receiving measurements or fluid mechanics data relating to the heart of a subject for all or part of the pacing settings of the set;
  estimating hemodynamic forces parameters by elaborating such measurements or inputting hemodynamic forces parameters as received;
  estimating hemodynamic forces parameters in the heart of the subject by elaborating such hemodynamic forces;
  selecting an optimal pacing setting of the set, or calculating further pace settings, based on the hemodynamic forces parameters as estimated A corresponding device and computer program are also disclosed.

12 Claims, 6 Drawing Sheets

(56) References Cited

U.S. PATENT DOCUMENTS

| | | | | |
|---|---|---|---|---|
| 2012/0041318 | A1* | 2/2012 | Taylor | G06T 7/13 600/504 |
| 2012/0283564 | A1* | 11/2012 | Ebbini | A61B 5/026 |
| 2014/0275961 | A1 | 9/2014 | Kassab | |
| 2014/0316758 | A1* | 10/2014 | Yagi | G06F 17/5009 703/9 |
| 2015/0164468 | A1* | 6/2015 | Ahn | G06V 10/44 600/504 |
| 2016/0140730 | A1* | 5/2016 | Falahatpisheh | G06V 10/42 |
| 2016/0228190 | A1* | 8/2016 | Georgescu | A61B 8/065 |
| 2016/0317816 | A1* | 11/2016 | Winter | A61N 1/36585 |
| 2017/0071567 | A1* | 3/2017 | Shibata | A61N 1/36842 607/18 |

OTHER PUBLICATIONS

International Search Report, PCT/EP2017/025269, dated Jun. 5, 2018.

International Written Opinion, PCT/EP2017/025269, dated Jun. 5, 2018.

Cardiac Fluid Dynamics Anticipates Heart Adaptation, Journal of Biomechanics, Pergamon Press, New York, NY, vol. 48, No. 2, Dec. 9, 2014, pp. 388-391.

Relationship between improvement in left ventricular dyssynchrony and contractile function and clinical outcome with cardiac resynchronization therapy: the MADIT-CRT trial. Eur Heart J 2011;32:1720-9.

Left Ventricular pacing vector selection by novel Echo-PIV analysis for optimization of quadripolar cardiac resynchronization device: a case report. Journal of Medical Case Reports 2016; 10:191.

Mechanical discoordination rather than dyssynchrony predicts reverse remodeling upon cardiac resynchronication. Am J. Physiol Heart Circ Physiol 2008;295:H640-6.

Agreement is poor among current criteria used to define response to cardiac resynchronization therapy. Circulation 2010;121:1985-1991.

In Vivo Analysis of Intraventricular Fluid Dynamics in Healthy Hearts. European Journal of Mechanics B/Fluids 2012; 35:40-46.

Two-Dimensional Intraventricular Flow Mapping by Digital Processing Conventional Color-Doppler Echocardiography Images. IEEE Trans Med Imag 2010;29:1701-1713.

Dyssynchrony, Contractile Function, and Response to Cardiac Resynchronizatiopn Therapy Circ Heart Failure 2011;4:433-40.

Hemodynamic Forces in a Model Left Ventricle. Phys Rev Fluids 2016 1 083201, doi:10.1103/PhysRevFluids. 1.083201.

The vortex—an early predictor of cardiovascular outcome, nature reviews cardiology 2014; 11:545-53.

Cardiac Fluid Dynamics Anticipates Heart Adaptation. J Biomech 2015; 48:388-391.

Changes in electrical activation modify the orientation of left ventricular flow momentum: novel observations using Echocardiographic Particle Image Velocimetry. Eur Heart J. Cariovasc Imag 2016; 17:203-209.

On estimating intraventricular hemodynamic forces from endocardial dynamics: a comparative study with 4D flow MRI. J Biomech 2017. DOI:10.1016/j.jbiomech.2017.06.046.

Left ventricular hemodynamic forces as a marker of mechanical dyssynchrony in heart failure patients with left bundle branch block. Scientific Reports 2017;7:2971.

Assessment of left ventricular hemodynamic forces in healthy subjects and patients with dilated cardiomyopathy using 4D flow MRI. Physiological reports 2016; 4:e12685.

Long-Term Trends in the Incidence of and Survival with Heart Failure, N Engl. J. Med 2002; 347:1397-1402.

Intraventricular pressure gradients in heart failure. Physiol Res 2013;62:479-487.

Tissue Tracking Technology for Assessing Cardiac Mechanics. JACC Imaging 2015; 12:1444-60.

Left and right ventricular hemodynaic forces in healthy volunteers and elite athletes assessed with 4D flow magnetic resonance imaging. AJP—Heart and Circ 2016. doi:10.1152/ajpheart.00583.2016.

* cited by examiner

METHOD AND DEVICE FOR CARDIAC ELECTRIC SYNCHRONIZATION

The disclosure relates to a method, a computer program and a system for determining optimal pacing settings in Cardiac electric Resynchronization Therapy (CRT) using conventional catheters or new quadripolar and multipolar catheters.

Heart failure (HF) is the principal social threatening cardiac progressive dysfunction. It presents either as a primary pathology or as consequence of numerous primary diseases. The clinical syndrome of heart failure is associated with the development of ventricular remodeling: a modification of ventricular geometry that progressively alters its functional parameters. Remodeling represents physiologic feedback that often does not lead to a stable configuration rather to a progressively worsening of the cardiac function and to failure. Despite modern treatments, hospitalization and death rate remains high, with nearly 50% of people diagnosed with heart failure dying within 5 years [1].

In a large number of patients affected by heart failure, pathologies are associated with impaired electrical conduction within the myocardium and typically a left bundle branch block (LBBB) that gives rise to the improper contraction. In this condition, the myocardium contracts in an uncoordinated, asynchronous manner; for example, it contracts in one region while it expands in another and gives little net flux of blood in the circulation. Therefore, one important therapeutic approach to heart failure is the cardiac resynchronization therapy, or CRT, where the contraction is synchronized by electric stimulation. In CRT, two electrodes are typically positioned in right ventricle apex and in a vein adjacent to the left ventricle respectively or, more recently, multiple LV leads, and quadripolar leads are available. Quadripolar LV leads have four electrodes that can pace the LV wall at several locations, using multiple vectors along the lead or between right and left catheters and allow many possibilities of stimulation patterns. A proper electrical stimulation can achieve optimal contraction and successful therapy with positive long-term outcome and survival.

However, a relevant number of patients do not improve ventricular function after CRT and this is essentially because the highly variability of venous anatomy and technical problems in reaching the site or sites with most delayed contraction that, generally, is also the most adapt to obtain resynchronization, impede to pace the heart in the proper sites. In these cases, to circumvent the problem, a tailored interventricular stimulation sequence between the electrodes may allow to obtain an improvement when not a normalization of the pattern of cardiac contraction. For example, in the simple bi-ventricular pacemaker one has to set the atrio-ventricular (A-V) stimulation timing delay and the ventricular-ventricular (V-V) delay. In more modern pacemakers using quadripolar leads, the values to optimize increases from two value (A-V and V-V) to sixteen or more different pacing vectors.

In this context, once it is assumed that the lead positioning is performed at best, the choice of the pacing settings turns into the major critical element for effectiveness of the therapy. The problem is that the pattern of electrical stimulation is difficult to be standardized because of individual differences in heart geometry and function and because of the procedural differences described above. Therefore, setting an optimal electrical stimulation is normally not immediate.

Pacemaker are often provided with algorithms aimed to optimize electrical activation based on ECG traces only. However, most typically, the A-V is set to zero and the V-V is set to zero or chosen between a pair of standard values. As an alternative, some research trials were tempted to optimize the stimulation based on cardiac mechanics, by using complex measures about the synchrony of cardiac contraction. One example is the standard deviation of the time-to-peak of transversal strain (SDTTS); however, results were not satisfactory [2, 3]. Indeed, equating CRT effectiveness through measurements of regional mechanics could be limiting [4], because the normal regional motion is not perfectly synchronous or uniform, and optimal space-time contraction pattern is difficult to define.

At the present time, the rate of success of CRT remains low: from 30 to 50% patients—depending on the criteria used to define when a procedure is successful—do not respond to the therapy [5]. However, a significant number of patients not responding to CRT can be transformed to responders using different pace settings [6]. Therefore, it is an accepted fact that therapeutic efficacy could be substantially improved if the electric stimulation pattern was optimized. Unfortunately, current imaging methods, essentially based on wall deformation analysis, are not capable of a reliable detection of the most suitable device setting for synchronizing the contraction of the walls. If this difficulty is evident in biventricular stimulation using unipolar catheters, more relevant problems are encountered with the use of quadripolar catheters in which case the parameter to be considered is not only the timing of the stimulation interval but also which pair of electrodes is the most appropriate.

The direction to achieve pacing optimization could be looked through a different perspective. Consider that "heart function is about creating and sustaining blood motion", which is obtained through a proper contraction-relaxation timing of the myocardial muscle. Such a correct contraction pattern is surely variable individually but, in any case, must be able to create the proper intraventricular pressure gradients (IVPGs) that drive blood motion during both ventricular ejection and ventricular filling. Recently, several studies made by catheters or by 3D phase-contrast magnetic resonance imaging (usually referred as 4D Flow MRI) recognized that heart failure is characterized by an alteration of IVPGs in the blood [7, 8, 9, 10]. Based on these results, it was suggested to optimize CRT by analyzing the blood motion and looking at IVPGs, or to hemodynamic forces, that are the IVPGs integrated over the entire cardiac chamber, whose proper alignment along the ventricular axis corresponds to optimal LV function [11, 12, 13].

The evaluation of hemodynamic forces, however, is not practically feasible for CRT optimization. When it is not based on a catheter [7] it relies on complex imaging methods that are not easily combined with a pace-maker setting procedure. One method is echo-PIV [10,12,13], which requires infusion of ultrasound contrast agent and echocardiographic images of high quality. This approach depends on operator's expertise and presents a limited reproducibility; moreover, the infusion of contrast agent is often not feasible or it cannot be prolonged for the analysis of multiple settings. The most reliable method for blood flow imaging is 4D Flow MRI, whose complexity in both acquisition and post-processing does not allow the systematic comparison of different settings. Moreover, most pacemakers are not compatible with MRI, some are MRI-compatible but only when switched off.

The inventors surprisingly realized that it is not necessary a full accurate hemodynamic analysis to obtain good results rather a few parameters based on hemodynamics can be used to estimate the fundamental properties of hemodynamic forces to be optimized. The main pacing sequences are, in fact, always set up through ECG parameters according to the ESC Guidelines on cardiac pacing and cardiac resynchronization therapy as last published in the European Heart Journal (2013) 34, 2281-2329. Estimations of hemodynamic forces parameters, even if not accurate, could lead to a significant improvement of pacing settings, particularly if associated with an optimized procedure to find out the most effective results.

It is thus an object to provide for a method improving pacing settings which is simple, easy to be exploited and cost effective.

The invention reaches the aim with a computer implemented method comprising:
a) receiving a set of pacing settings for the pace maker;
b) receiving measurements or fluid mechanics data relating to the heart of a subject corresponding to all or part of the pacing settings of the set;
c) estimating hemodynamic forces parameters by elaborating such measurements or inputting hemodynamic forces parameters as received;
d) selecting an optimal pacing setting of the set, or calculating further pace settings, based on the hemodynamic forces parameters as estimated.

In an advantageous configuration, the last operation, or the entire procedure, if necessary, are repeated iteratively eventually progressively reducing the search region in the space of pacing setting parameters to converge to optimal solution.

To such extent, step d) may comprise selecting one or more pacing settings of the set or building a different pacing setting based on an optimization process, particularly through a either unconstrained or constrained minimization/maximization process methods.

In an embodiment, step d) is extended into an iterative procedure comprising:
d.1) calculating a new setting as a tentative optimal setting;
d.2) adding the new setting to the set of pacing settings;
d.3) receiving measurements or fluid mechanics data relating to such new setting;
d.4) estimating hemodynamic force parameters for the new setting by elaborating measurements for the new setting or input hemodynamic forces parameters as received for the new setting;
d.5) improve selection of an optimal pacing setting, or calculating further pace settings, based on the new hemodynamic forces parameters as estimated.
d.6) repeat from steps d.1 until optimization of a cost function based on one or more parameters with a stop criteria based on a minimal variation in the value of the optimized parameters.

This allows to operate the choice not only among already available settings, but on a set that is built dynamically during the procedure leading to a very powerful software tool for improving CRT.

According to an aspect, there is a computer product directly loadable in the memory of a digital computer and comprising software code portions for performing the method according to embodiments herein when the product is run on a computer.

According to another aspect, there is a device for improving pacing settings of a pace maker for a subject, comprising:
a first input for receiving measurements of data relating to the heart of the subject;
a second input for receiving a set of pacing settings for the pace maker;
a processing unit;
an output,
wherein such processing unit is configured to:
estimate hemodynamic forces parameters induced in the heart when the pacing settings are adopted by the pace maker by elaborating such measurements of data;
select one or more optimal pace settings of the set, or elaborate further pace settings, based on the calculated/input hemodynamic forces parameters;
output the selected or elaborated pace setting or settings.

The device can advantageously operate in iterative mode with the processing unit performing the method steps as seen above to elaborate a dynamic set of pacing settings.

Further improvements of the invention will form the subject of the dependent claims.

The characteristics of the invention and the advantages derived therefrom will be more apparent from the following description of non-limiting embodiments, illustrated in the annexed drawings, in which.

The device of the present invention lends itself to many embodiments. They may often differ from the way hemodynamic forces are obtained. Indeed intraventricular pressure can be directly measured or, more typically, velocities can be received from measurements and imaging technology. From one or more velocity/acceleration values it is then possible to estimate the hemodynamic force, that is the pressure gradients integrated in the cardiac cavity of volume V(t), by inversion of the Navier-Stokes equation as follows $$F(t) = \int_{V(t)} \rho \left( \frac{\partial v}{\partial t} + v \cdot \nabla v \right) dV$$

where the integral can be evaluated numerically by an appropriate quadrature formula, among the numerous available, depending on the spatial distribution and properties of the available measurements.

Figure 1:
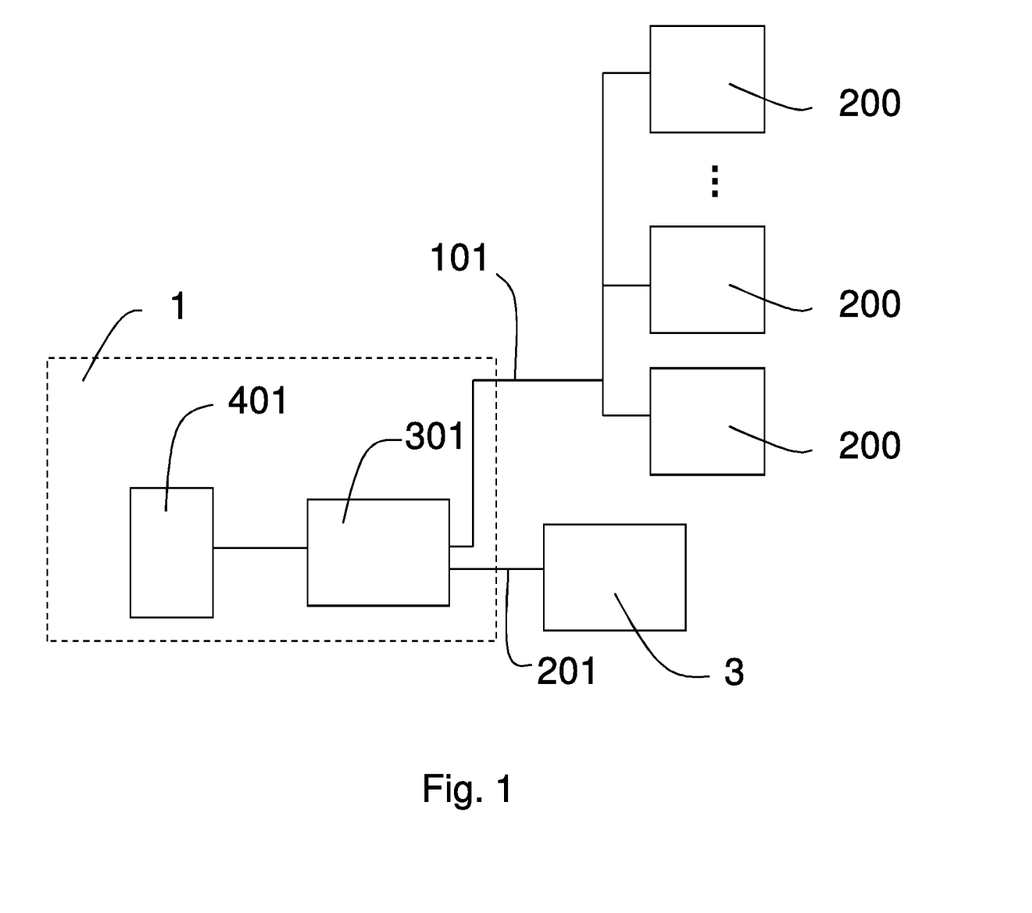
FIG. 1 illustrate exemplified block diagram of a first embodiment of the device.

In the form shown in FIG. 1, the device 1 is provided in combination with a plurality of sensors 200, particularly micro-probes. capable of detecting velocity, displacement, pressure, acceleration or the like parameters at few points of the heart, particularly the left ventricle of a patient and provide such parameters at an input 101 of the device.

Indeed, the CRT procedure requires the implant of pacing leads; therefore, during the same procedure, other micro-sensors can be introduced as additions or as part of the same pacing equipment. Nowadays, the micro-sensors technology provides availability of numerous micro-measurement tools. Such sensors can be pressure micro- or nano-transducers placed close to the endocardial epithelium or hidden inside the trabeculae, thus providing direct measures of pressure differences. Such micro-sensors can also be accelerometers, from which the velocity can be obtained by time integration, or they can be position sensors, from which the velocity can be obtained by time differentiation. From the position sensor also the dimension of the cardiac cavity can be estimated allowing to improve the quadrature formulas as in [15]. From pressure micro-transducers the actual pressure can be obtained. All technologically available micro-sensors information can be integrated to provide robust estimates of the intraventricular pressure gradient based on known basic principles of physics In the embodiment shown in FIG. 2, the device 1 is provided in combination with an ultrasound apparatus 2 having at least a probe 4 for acquiring Doppler information of a plurality of points in the heart, particularly the left ventricle, of the subject. This allows to input velocity vector components of a plurality of points in the heart without the need of invasive devices.

Figure 2:
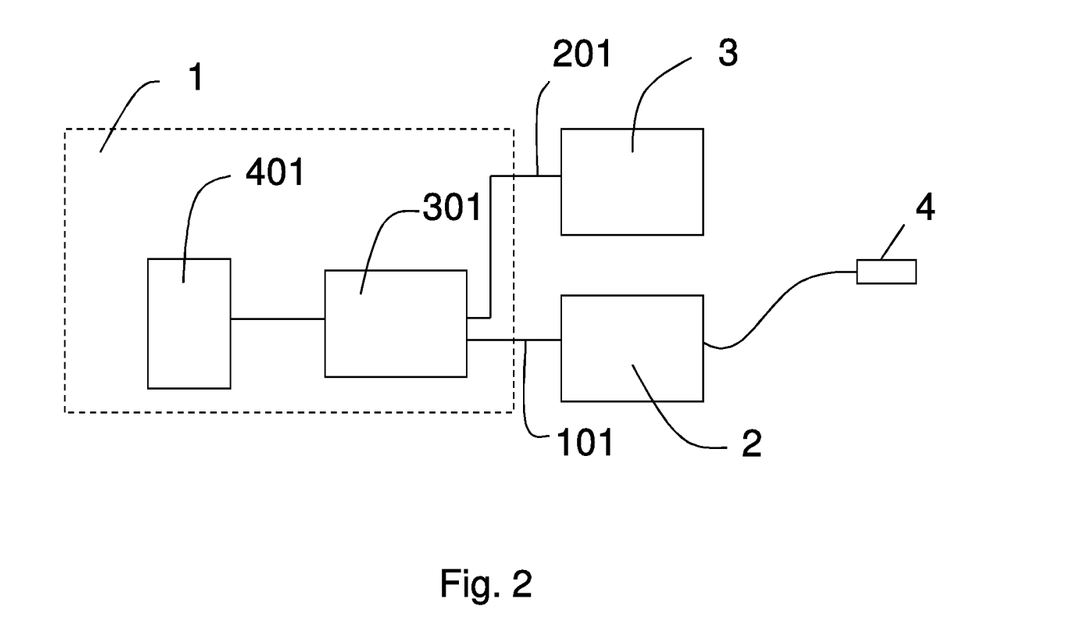
FIG. 2 illustrates an exemplified block diagram of a second embodiment of the device.

If the ultrasound apparatus is an echographic apparatus 2 sequences of data of the heart of a patient in the form of bi-dimensional or three-dimensional images can be acquired. These data provided at the input 101 allow to evaluate the dynamics of the endocardial border and the flux of momentum across the mitral and aortic valves of the subject. The apparatus 2 is connected in a physical manner or through wireless or Ethernet computer connections, to an input 101. It is also possible to provide that the exchange of data between apparatus 2 and device 1 is carried out through mass memories or in a way completely independent from the operation mode of the echographic apparatus 2 that, for this reason, can be of any type.

All the embodiments comprise a processing unit 301 that reads the input data and process them to estimate hemodynamic forces parameters in the heart of the patient by performing one or more steps of the method according to embodiments herein. An output, for example in form of a monitor 401, can show the results of the analysis in graphics and/or numeric form. The processing unit 301 may be a dedicated microprocessor system or, more generally, a PC also of the general purpose type. The characteristics of the unit 301 will obviously reflect on the processing speed.

The device also comprises a further input 201 for receiving a set of pacing settings for the pace maker 3. This allows the processing unit 301 to calculate hemodynamic forces parameters for each setting.

Alternatively or in combination, hemodynamic forces parameters for each pacing setting can be an input with the device operating to select or build a specific pacing setting for the patient.

Figure 4:
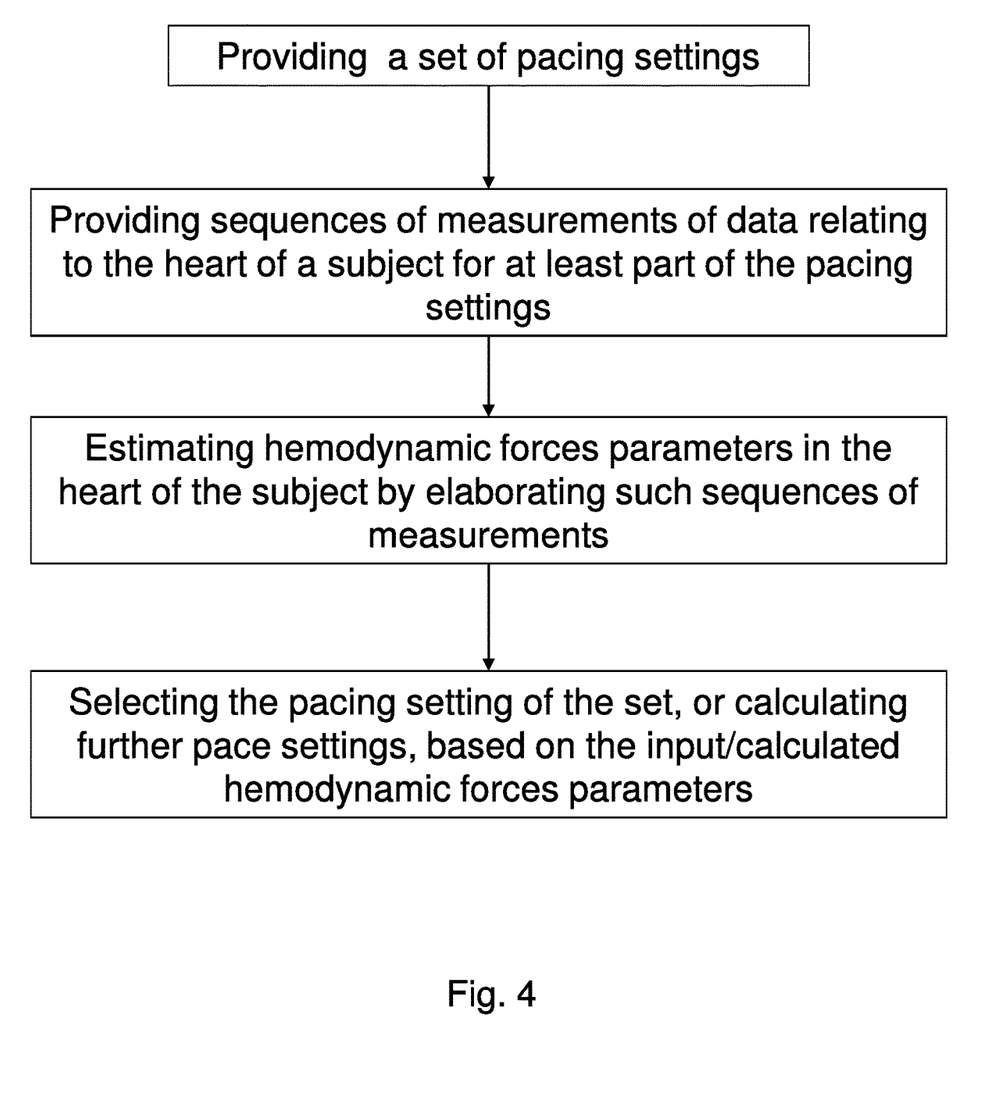
FIG. 4-6 illustrate a flowchart of the operations of methods according to embodiments herein.
Figure 5:
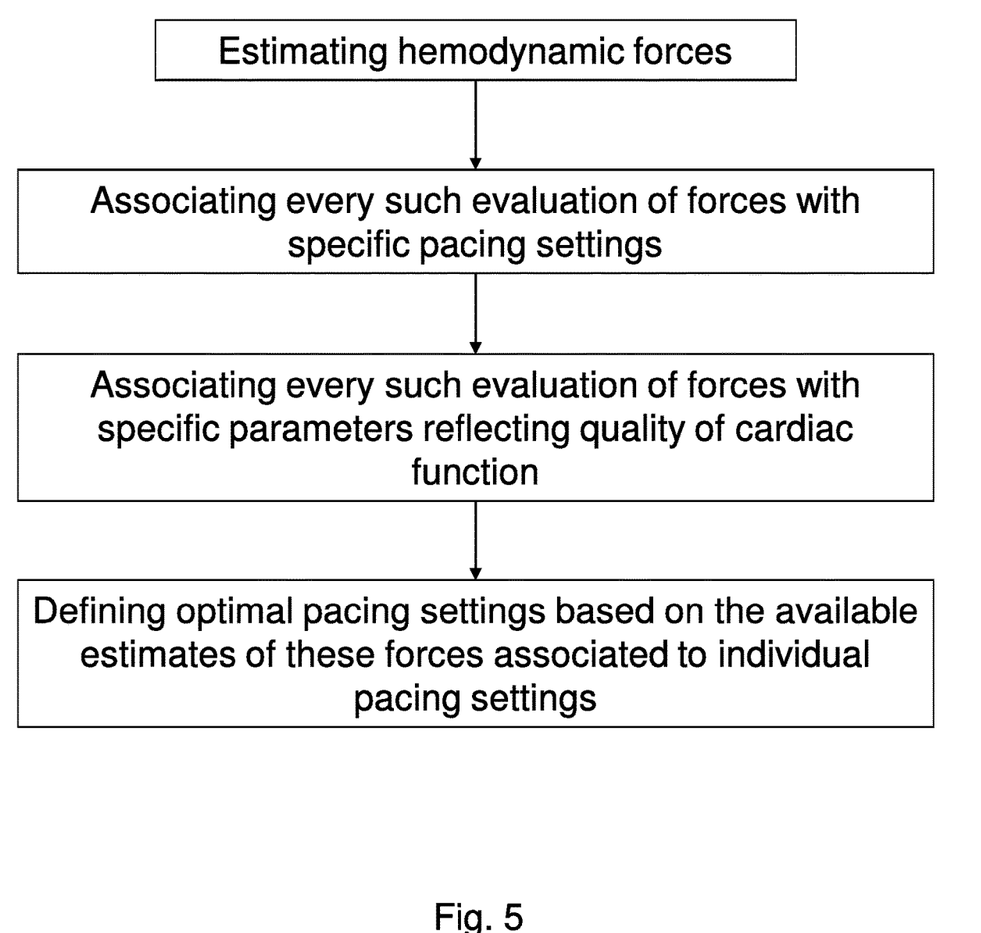
Figure 6:
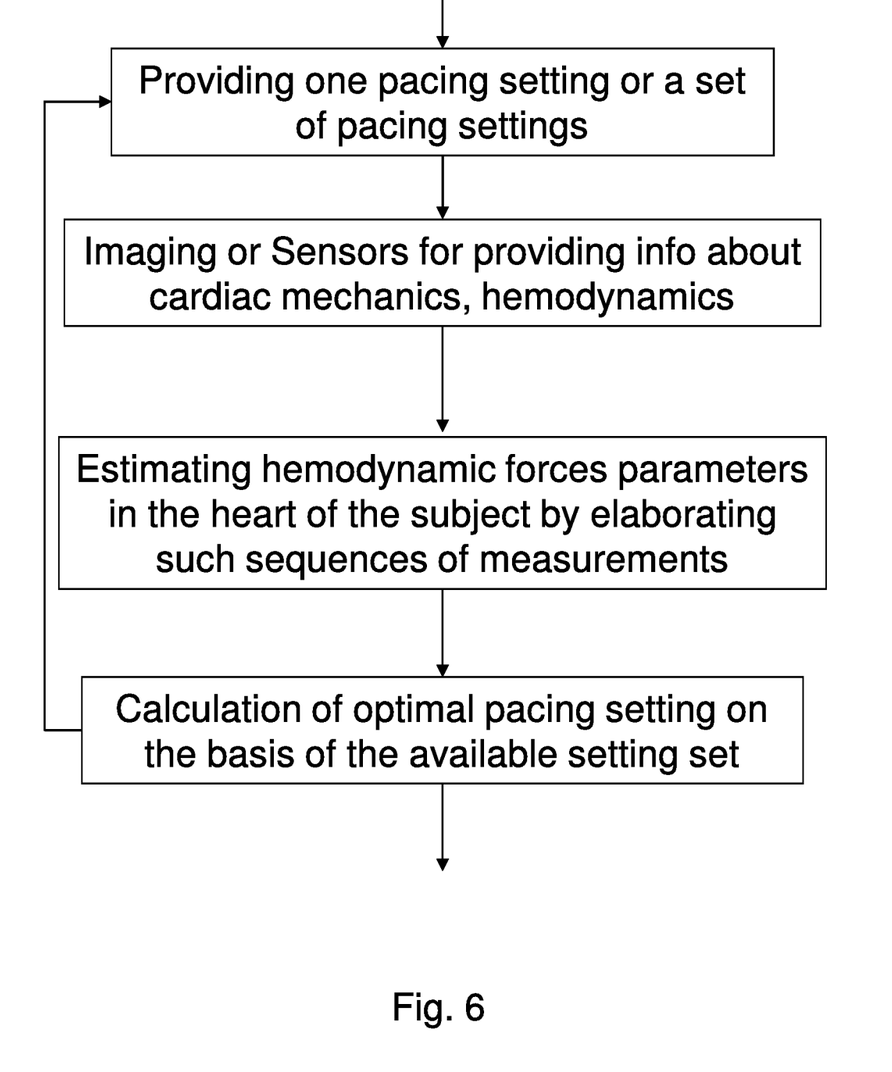

Depending on the type of data available at the input, the processing unit 301 is configured to elaborate data information of the heart of a subject to estimate hemodynamic forces parameters and, thus, determine an appropriate pacing setting by performing the operations as shown in the flowchart of FIGS. 4 to 6.

With reference to the flowchart of FIG. 5, an embodiment comprises four basic operations:

(A) estimating hemodynamic forces in a reproducible manner;

(B) associating every such evaluation of forces with specific pacing settings and (C) associating every such evaluation of forces with specific parameters reflecting quality of cardiac function and (D) defining optimal pacing settings based on the available estimates of these forces associated to individual pacing settings.

(A) Hemodynamic Forces Estimation.

In general, this passage represents a whatsoever method to find an estimate, or a surrogate, or an approximation of hemodynamic forces. This can be achieved from several means combining data of cardiac mechanics that can be get from ultrasound imaging, from 3D imaging to punctual measures, or from measures of micro-sensors. All these methods have the common result of achieving an estimate, or a surrogate, or an approximation of hemodynamic forces:

One method to estimate hemodynamic forces is based on the knowledge of the dynamics of the endocardial border and flux of momentum across the valves using the mathematical model described in [15]. This thus requires (A1) a mean to record and/or visualize 3D or multiplane ultrasound imaging, (A2) a mean to evaluated endocardial dynamics like speckle tracking and/or border detection either automatic or manual; (A3) a mean to estimate the effective valvular orifice area. This part of the whole system must also be characterized by a clear driven workflow that minimizes the operator dependency that may otherwise appear using general purpose tools in the evaluation of different ultrasound recording.

A minimum image record is envisaged as that of an apical 3-chamber that allows the visualization of mitral inflow and ventricular outflow tract and where an estimation of the 3D geometry can be obtained by symmetry assumptions.

Another method to estimate hemodynamic forces is based on the knowledge of the fluid dynamics inside the ventricular cavity by mean of ultrasound methods.

This thus requires (A1) a mean to record and/or visualize 2D or 3D Doppler ultrasound imaging, (A2) a mean to transform Doppler ultrasound information into a multidimensional velocity field [17, 18, 19] and eventually into a pressure gradient field [20]. This part of the whole system must also be characterized by a clear driven workflow that minimizes the operator dependency that may otherwise appear using general purpose tools in the evaluation of different ultrasound recording.

A simpler method to estimate hemodynamic forces is based on the knowledge of the velocity at a few points inside the cardiac chamber. This thus requires (A1) a mean to record and/or visualize the velocity at one or a few points, or along a line, by (PW/CW/M-Color) Doppler ultrasound, (A2) a mean to evaluated pressure gradients from the individual velocity fields. This can be typically achieved from inversion of the Navier-Stokes equation and evaluating the pressure gradient, or the total force including or not the friction effects, from the appropriate velocity variations in time and, when available, in space.

For example, even from a single velocity measurement $V_{MV}(t)$ in the mitral jet the diastolic pressure gradient can be estimated by integrating Navier-Stokes from that basal point and a point at the apex where velocity is approximately null. This balance provides the IVPG from base to apex as $$\Delta p(t) = -\frac{\rho}{2}\frac{\partial V_{MV}}{\partial t}H - \rho\frac{v_{MV}^2}{2}$$

where H is the height of the ventricle, and we have assumed a linear spatial variation in velocity. Then, the hemodynamic force can be estimated by a simple quadrature given by this IVPG multiplied by the mean cross sectional area of the ventricle. Or, the normalized hemodynamic force divided by the ventricular volume can be estimated by a simple quadrature given by this IVPG divided by the ventricle height H. More accurate weighted quadrature techniques can be used by properly accounting for the shape of the ventricular chamber.

When more measurement points are available the same approach can be used and the integral are performed by more accurate numerical quadrature techniques.

Similarly, other approaches for estimating IVPGs can be developed from measures of velocity, or displacement, or pressure at one or few points through micro-probes about the left ventricle. All technologically available micro-sensors' information can be integrated to provide robust estimates of the intraventricular pressure gradient based on known basic principles of physics.

(B) Evaluation of Hemodynamic Parameters of Cardiac Function

The such obtained hemodynamic forces are time-varying vectors, sometime vector fields, that require a parametrization into one or few parameters to create a space of parameters of small enough dimension that allows optimization from the limited information available. Typically, the forces must be mainly directed along the longitudinal (base-to-apex) direction; they must be strong enough to ensure efficient cardiac function, they must be balanced and so on.

Significant hemodynamic parameters can thus be created following such concepts. Several parameters can be created this way on the basis of fundamental understanding of correct fluid dynamics for cardiac function. One example is the ratio between the transversal and longitudinal components of the spatially averaged hemodynamic force, which must be as small as possible for normal filling-emptying mechanism across the base. A second example is the entity of the longitudinal force, possibly normalized with the cardiac chamber volume, that must be maximized for efficient function. Another example is the center of application of the hemodynamic force, which should be in the center of the cavity for best balance. A further example is the torque given by the hemodynamic forces that is expected to be close to zero in normal function to avoid non-physiological rotational stresses to the cardiac chamber. All these parameters are still time profiles from which single measures can be obtained from peak or root-mean-square values evaluated during the entire cardiac cycle or specified intervals, like systole or diastole or portions/combinations thereof. Best suited parameters, possibly depending on subject-specific pathological conditions, will be individuated along with clinical experience.

(C) Association of Pacing Settings to Force Evaluation

The specific pacing settings can be introduced manually into the external optimization device every time a force measurement is performed. The device can also be part of the external pacing driver itself that sets the pacing settings. In this way, the settings are inherently given by the device itself or acquired when they are communicated to the implanted pace-maker.

In another approach, the measurement device, like an imaging system with processing unit, can be integrated, in regular dimension or miniature, within the pacing system that automatically associates pacing and hemodynamic parameters.

In a more integrated approach the device can be in miniature and be included internally as part of the implanted pace-maker itself, in which case the settings are inherently available to the integrated system.

(D) Optimization

The device may include a method to extract the optimal pacing settings. In a basic simplest method, optimal pacing settings can be defined as those associated with optimal measured value of a chosen hemodynamic force parameter, for example the setting associated with the most aligned and/or highest base-apex component. Another simple option is that of an interpolation of parameters among the measured ones and seek the minimum of the interpolated function, allowing to detect optimal setting in between the measured ones. However, more advanced optimization procedures can be implemented. Indeed, the force measurements can be initially limited to few tentative setting options, whereas the optimal setting can be another value not present in the original starting set. This suggests using an optimization procedure, possibly, but not necessarily, of the iterative type, for detecting the most effective result with a stop criteria, for example, based on a minimal variation in the value of one or more parameters in a different tentative or consecutive iterations. Optimization in this case can include those falling in the category of constrained optimization that is essentially that of finding the minimum, or maximum, of a target function subjected to some constraints. Constraints in this case can be the periodicity of the function, that some delay cannot be negative, that some delay cannot be larger than another, that none can be larger than the duration of systole; specific constraint depending on the specific pace-maker utilized.

Constrained minimization can be achieved by very numerous means, one famous example is the method of Lagrange multipliers, but numerous other methods can be employed.

In the basic embodiment the device can be integrated in the external system used at the time of CRT optimization, for example after the implant or at any periodic follow-up. Integrating the pace-maker procedure with such a device would permit to optimize the CRT and largely improve the therapeutic outcome.

In a further advanced embodiment, the miniature device can be integrated in the pace-maker itself, particularly when the implant includes measurements micro-sensors that permit to estimate the hemodynamic forces. In this case, the optimization of the setting can be performed with more ease without the need of an external system.

This same integrated miniature embodiment can even allow the optimization of the setting totally integrated in the pacing system. Thus optimization can be performed in real-time or quasi-real-time by the pacing device itself, thus allowing a continuous optimal pacing.

To such extent an embodiment provides for a pace-maker comprising, an input for receiving pacing settings, a memory for storing at least one pacing setting, pacing means for actuating a pacing sequence on the basis of the pacing setting stored in the memory and a device according to embodiments herein. The pace-maker and the device are arranged so that the second input 201 of the device receives the pacing setting or settings of the pace-maker and the output 401 of the device 1 transmits the optimized pacing setting to the input of the pace-maker when the processing unit 301 of the device 1 performs one or more steps of the method according to embodiments herein.

Figure 3:
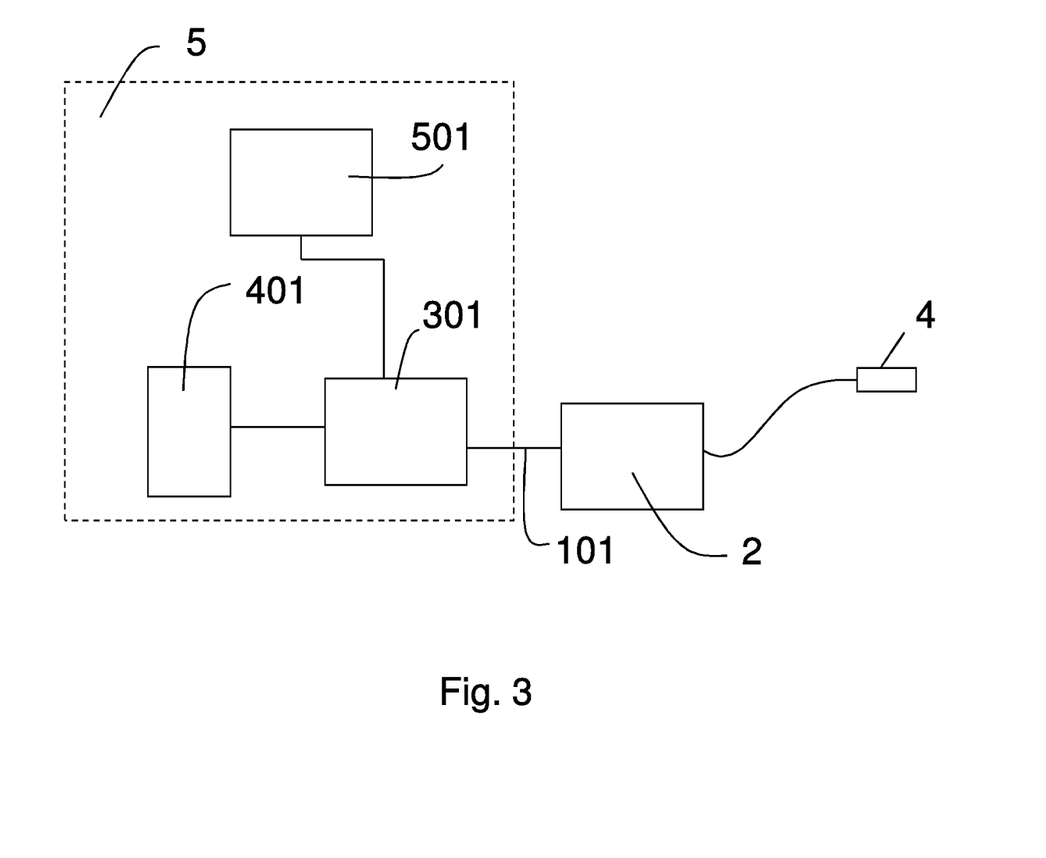
FIG. 3 illustrates an exemplified block diagram of a third embodiment of the device.

The device can also be integrated in the pace-maker as exemplary shown in FIG. 3 (for the configuration with an ultrasound apparatus 2) so that the processing unit 501 of the pace-maker 5 can execute one or more operations of the method according to embodiments herein thus realizing a very compact system capable to adjust the pacing setting on the basis of hemodynamic forces as directly estimated also when the pace-maker is in operation.

REFERENCES

[1] Levy D, Kenchaiah S, Larson M G, Benjamin E J, Kupka M J, Ho K K L, Murabito J M, Vasan R S. Long-Term Trends in the Incidence of and Survival with Heart Failure. N Engl J Med 2002; 347:1397-1402.

[2] Knappe D, Pouleur A C, Shah A M, Cheng S, Uno H, Bourgoun M et al. Dyssynchrony, Contractile Function, and Response to Cardiac Resynchronization Therapy. Circ Heart Failure 2011; 4:433-40.

[3] Pouleur A C, Knappe D, Shah A M, Uno H, Bourgoun M, Foster E et al. Relationship between improvement in left ventricular dyssynchrony and contractile function and clinical outcome with cardiac resynchronization therapy: the MADIT-CRT trial. Eur Heart J 2011; 32:1720-9.

[4] Kirn B, Jansen A, Bracke F, van Gelder B, Arts T, Prinzen F W. Mechanical discoordination rather than dyssynchrony predicts reverse remodeling upon cardiac resynchronization. Am J Physiol Heart Circ Physiol 2008; 295:H640-6.

[5] Fornwalt B K, Sprague W W, BeDell P, et al. Agreement is poor among current criteria used to define response to cardiac resynchronization therapy. Circulation 2010; 121: 1985-1991.

[6] Martiniello A R, Pedrizzetti G, Bianchi V, Tonti G, D'Onofrio A, Caso P. Left ventricular pacing vector selection by novel Echo-PIV analysis for optimization of quadripolar cardiac resynchronization device: a case report. Journal of Medical Case Reports 2016; 10:191.

[7] Guerra M S, Bra's-Silva C, Amorim M J, Moura C, Bastos P, Leite-Moreira A F. Intraventricular pressure gradients in heart failure. Physiol Res 2013; 62:479-487

[8] Arvidsson P M, Töger J, Carlsson M, Steding-Ehrenborg K, Pedrizzetti G, Heiberg E, Arheden H. Left and right ventricular hemodynamic forces in healthy volunteers and elite athletes assessed with 4D flow magnetic resonance imaging. AJP-Heart and Circ 2016. doi:10.1152/ajp-heart.00583.2016.

[9] Eriksson J, Bolger A F, Ebbers T, Carlhäll C J. Assessment of left ventricular hemodynamic forces in healthy subjects and patients with dilated cardiomyopathy using 4D flow MRI. Physiological reports 2016; 4:e12685

[10] Pedrizzetti G, La Canna G, Alfieri O, Tonti G. The vortex—an early predictor of cardiovascular outcome. nature reviews cardiology 2014; 11:545-53.

[11] Eriksson J, Zajac J, Alehagen U, Bolger A F, Ebbers T, Carlhäll C J. Left ventricular hemodynamic forces as a marker of mechanical dyssynchrony in heart failure patients with left bundle branch block. Scientific Reports 2017; 7:2971

[12] Pedrizzetti G, Martiniello A R, Bianchi V, D'Onofrio A, Caso P, Tonti G. Cardiac Fluid Dynamics Anticipates Heart Adaptation. J Biomech 2015; 48:388-391.

[13] Pedrizzetti G, Martiniello A R, Bianchi V, D'Onofrio A, Caso P, Tonti G. Changes in electrical activation modify the direction of left ventricular flow momentum: novel observations using Echocardiographic Particle Image Velocimetry. Eur Heart J, Cardiovasc Imag 2016; 17:203-209.

[14] Domenichini F, Pedrizzetti G. Hemodynamic Forces in a Model Left Ventricle. Phys Rev Fluids 2016 1 083201, doi:10.1103/PhysRevFluids.1.083201.

[15] Pedrizzetti G, Arvidsson P M, Töger J, Borgquist R, Domenichini F, Arheden H, Heiberg E. On estimating intraventricular hemodynamic forces from endocardial dynamics: a comparative study with 4D flow MRI. J Biomech 2017. DOI:10.1016/j.jbiomech.2017.06.046

[16] Claus P, Omar A M S, Pedrizzetti G, Sengupta P P, Nagel E. Tissue Tracking Technology for Assessing Cardiac Mechanics. JACC Imaging 2019; 12:1444-60.

[17] Garcia D, del Álamo J C, Tanné D, Yotti R, Cortina C, Bertrand É, Antoranz J C, Pérez-David E, Rieu R, Fernández-Aviles F, Bermejo J. Two-Dimensional Intraventricular Flow Mapping by Digital Processing Conventional Color-Doppler Echocardiography Images. IEEE Trans Med Imag 2010; 29:1701-1713.

[18] Ohtsuki S, Tanaka M. Method to estimate planar flow from Doppler velocity distribution in an observation plane. U.S. Pat. No. 5,947,903; Sep. 7, 1999.

[19] Pedrizzetti G, Tonti G. Method of transforming a Doppler velocity field into a velocity vector field. U.S. Pat. No. 8,858,437.

[20] Cimino S, Pedrizzetti G, Tonti G, Canali E, Petronilli V, De Luca L, Iacoboni C, Agati L. In vivo Analysis of Intraventricular Fluid Dynamics in Healthy Hearts. European Journal of Mechanics B/Fluids 2012; 35:40-46.

The invention claimed is:

1. Method for improving pacing settings of a pace maker, comprising, by means of a processing unit:
   a) receiving a set of pacing settings for the pace maker;
   b) receiving measurements or fluid mechanics data relating to a heart of a subject for all or part of the pacing settings of the set;
   c) estimating hemodynamic force parameters by elaborating such measurements or input hemodynamic forces parameters as received;
   d) selecting an optimal pacing setting of the set, or calculating further pace settings, based on the hemodynamic forces parameters as estimated; and
   e) updating the pacing settings of the pace maker with the optimal pacing setting or calculated further pace settings;
   wherein b) and c) are executed as one or more of:
   b) comprising providing pressure information of a plurality of points in the left ventricle of the subject, and c) comprising transforming the pressure information into a pressure difference or gradient field inside the left ventricle;
   b) comprising providing acceleration or position information of a plurality of points in the left ventricle of the subject, and c) comprising transforming the acceleration/position information into velocity information by time integration/derivation and evaluating pressure gradients from such velocities by integrating the Navier Stokes equation;
   b) comprising providing a velocity at a plurality of points inside the cardiac chamber and c) comprising evaluating pressure gradients from such velocities by integrating the Navier Stokes equation;
   b) comprising providing bi-dimensional or tri-dimensional Doppler ultrasound information of the left ventricle of the subject, and c) comprising transforming the Doppler ultrasound information into a multidimensional velocity field and calculating from the multidimensional velocity field a pressure gradient field inside the left ventricle; and
   b) comprising providing dynamics of the endocardial border and flux of momentum across the mitral and aortic valves of the subject, and c) comprising calculating hemodynamic forces as those required to balance the flux of momentum across the mitral and aortic valves and the force absorbed by the myocardium.

2. Method according to claim 1, wherein d) comprises selecting one or more pacing settings of the set or building a different pacing setting based on an optimization process.

3. Method according to claim 1, wherein d) is repeated iteratively by progressively reducing a search region in a space of pacing setting parameters to converge to optimal solution.

4. Method according to claim 1, wherein d) is extended into an iterative procedure comprising:
- d.1) calculating a new setting as a tentative optimal setting;
- d.2) adding the new setting to the set of pacing settings;
- d.3) receiving measurements or fluid mechanics data relating to such new setting;
- d.4) estimating hemodynamic force parameters for the new setting by elaborating measurements for the new setting or input hemodynamic forces parameters as received for the new setting;
- d.5) improve selection of an optimal pacing setting, or calculating further pace settings, based on the new hemodynamic forces parameters as estimated; and
- d.6) repeat d.1) to d.5) until optimization of a cost function based on one or more parameters with a stop criteria based on a minimal variation in a value of optimized parameters.

5. Method according to claim 1, wherein d) comprises selecting or elaborating pacing settings associated with a most aligned and/or highest base-apex component.

6. Method according to claim 1, wherein c) comprises estimating one or more parameters selected from a group comprising: a ratio between the transversal and longitudinal components of a spatially averaged hemodynamic force, an entity of the longitudinal force, a center of application of a hemodynamic force, and a torque given by a hemodynamic force.

7. Method according to claim 1, wherein b) comprises providing velocity, acceleration, displacement or pressure information of a plurality of points in the heart.

8. Method according to claim 1, wherein:
- b) comprises providing the velocity at a plurality of points inside the cardiac chamber and c) comprises evaluating pressure gradients from such velocities by integrating the Navier Stokes equation; and
- from the velocity measurement in a mitral jet ($V_{MV}$), a diastolic pressure gradient ($\Delta p$) is estimated by integrating, from a basal point to a point at an apex having a substantially null velocity, assuming a linear spatial variation in velocity, the equation:

$$\Delta p(t) = -\frac{\rho}{2}\frac{\partial V_{MV}}{\partial t}H - \rho\frac{v_{MV}^2}{2}$$

where H is the height of the ventricle and $\rho$ is blood density.

9. Method according to claim 1, wherein c) comprises evaluating pressure gradients from such velocities by integrating the Navier Stokes equation; and
- the integration of the Navier-Stokes equation is performed with numerical quadrature techniques.

10. Method according to claim 1, wherein:
- b) comprises providing the dynamics of the endocardial border and flux of momentum across the mitral and aortic valves of the subject;
- c) comprises calculating hemodynamic forces as those required to balance the flux of momentum across the mitral and aortic valves and the force absorbed by the myocardium; and
- single measure parameters are obtained from a norm of the hemodynamic force, from an infinite-norm or peak value to a 2-norm or root-mean-square value, evaluated during an entire cardiac cycle or specified intervals thereof.

11. A computer product directly loadable in a memory of a digital computer and comprising software code portions for performing the method according to claim 1 when the product is run on a computer.

12. Method for improving pacing settings of a pace maker, comprising, by means of a processing unit:
- e) receiving a set of pacing settings for the pace maker;
- f) receiving measurements or fluid mechanics data relating to a heart of a subject for all or part of the pacing settings of the set;
- g) estimating hemodynamic forces by elaborating such measurements or input hemodynamic forces as received;
- h) estimating hemodynamic force parameters from the hemodynamic forces; and
- i) selecting an optimal pacing setting of the set, or calculating further pace settings, based on the hemodynamic forces parameters as estimated; and
- j) updating the pacing settings of the pace maker with the optimal pacing setting or calculated further pace settings.

* * * * *